United States Patent
Brugnoli

(10) Patent No.: US 6,206,837 B1
(45) Date of Patent: Mar. 27, 2001

(54) PORTABLE SYSTEM WITH TELEMETRIC DATA TRANSMISSION FOR THE MEASUREMENT OF METABOLIC PARAMETERS

(76) Inventor: Paolo Brugnoli, viale della Vittoria 21, 00122 Roma (IT)

( * ) Notice: Subject to any disclaimer, the term of this patent is extended or adjusted under 35 U.S.C. 154(b) by 0 days.

(21) Appl. No.: 09/202,528

(22) PCT Filed: Jul. 31, 1997

(86) PCT No.: PCT/IT97/00197

§ 371 Date: Dec. 17, 1998

§ 102(e) Date: Dec. 17, 1998

(87) PCT Pub. No.: WO98/53732

PCT Pub. Date: Dec. 3, 1998

(30) Foreign Application Priority Data

May 27, 1997 (IT) .............................. RM97A0314

(51) Int. Cl.[7] .................................................. A61B 5/08
(52) U.S. Cl. .................. 600/529; 600/531; 600/538; 600/301
(58) Field of Search ...................... 600/529, 531, 600/532, 533, 538, 484, 301, 300, 508

(56) References Cited

U.S. PATENT DOCUMENTS

| 4,440,177 | * | 4/1984 | Anderson et al. | 600/532 |
| 4,909,259 | * | 3/1990 | Tehrani | 600/531 |
| 5,060,656 | * | 10/1991 | Howard | 600/531 |
| 5,117,674 | * | 6/1992 | Howard | 73/31.07 |
| 5,363,857 | * | 11/1994 | Howard | 600/531 |

FOREIGN PATENT DOCUMENTS

| 1466834A | 3/1969 | (DE) . |
| 196396A | 10/1986 | (EP) . |
| 369506A | 5/1990 | (EP) . |
| 760224A | 3/1997 | (EP) . |
| 2604888A | 4/1988 | (FR) . |
| 2258587A | 2/1993 | (GB) . |
| 6615576A | 5/1968 | (NL) . |

* cited by examiner

Primary Examiner—Max Hindenburg
Assistant Examiner—Navin Natnithithadha
(74) Attorney, Agent, or Firm—Smith, Gambrell & Russell, LLP

(57) ABSTRACT

A portable system for the measurement of the metabolic parameters of an individual, athlete or patient, in real conditions of physical activity, using a "breath by breath" technique. The portable system includes a portable unit (1) that has a reduced weight and dimensions, and is fixed to the body of the individual by means of an anatomic harness (2) during the test, a turbine flowmeter (3-4-8) applied at the mouth of the individual through an anatomic face mask (6-7-8), a heart rate monitor belt (10), a rechargeable battery (11) for supplying the system, and a receiver unit (12) that is connected to a personal computer (14) by RS232 connection (13), allowing the receipt and display of the measurement in real time on the screen.

The portable unit includes a fast $CO_2$ analyzer, an intrinsically slow oxygen analyzer, whose output signal is elaborated in order to obtain a response time short enough to allow the accurate measurements on a "breath by breath" basis, a microprocessor, a memory for data storage, a UHF transmitter, an LCD display, and a keyboard.

The receiver unit includes a UHF receiver module and an interface for the connection to the personal computer.

The flowmeter is a bidirectional turbine (3) and an optoelectronic reader that, based on the infrared interruption technique, detects the rotations of a blade and consequently the volumes ventilated by the individual.

14 Claims, 3 Drawing Sheets

PORTABLE SYSTEM WITH TELEMETRIC DATA TRANSMISSION FOR THE MEASUREMENT OF METABOLIC PARAMETERS

BACKGROUND OF THE INVENTION

The present invention consists of a portable system for the "breath by breath" measurement of the metabolic parameters of an individual, with telemetric data transmission and storage of results for further analysis.

It is known that, nowadays, the analysis of the metabolic response of an individual is usually performed in laboratories using stationary equipment able to measure mainly the following parameters: oxygen uptake ($VO_2$), carbon dioxide production ($VCO_2$), respiratory quotient ($RQ=VCO_2/VO_2$), ventilation (VE) and heart rate (HR).

These equipments allow testing to occur, with the use of an ergometer, while the individual performs a physical activity, such as cycling or using a treadmill.

The major limitation of the previously mentioned methodology is related to the fact that most of the activities (sports and non-sports) such as skiing, tennis, the daily job, or driving a wheelchair, cannot be correctly simulated in the lab.

Up to some years ago, portable systems for metabolic tests were not available. The device described in the U.S. Pat. No. 4,658,832 (BRUGNOLI), dated Apr. 21, 1987, was the first system with limited dimensions introduced into the market.

During the last years, however, the measurement techniques of the metabolic parameters used by the stationary systems has evolved, turning from the "mixing chamber" methodology to the "breath by breath" technique.

The first one, as it is well known, provides the results as an average of all the breaths carried out in a consistent time interval (typically 30 seconds), while the second one provides results for each breath of the individual.

The "breath by breath" analysis is described in detail in the following publications:
Beaver, Wasserman, Whipp, JAP. 34(1): 128–132, 1973 "On Line Computer Analysis and Breath by Breath Graphical Display of Exercise Function Tests";
Sue, Hansen, Blais, Wasserman, JAP, 49(3): 456–461, 1980: "Measurement and Analysis of Gas Exchange, Using a Programmable Calculator";
Wasserman et al. 1994: "Principles of Exercise Testing and Interpretation", $2^{nd}$ Edition.

The origin of the two previously mentioned techniques is related to a technological limitation: the measurement of the oxygen uptake ($VO_2$) and carbon dioxide production ($VCO_2$) in correspondence of each breath, requires the use of two gas analyzers with a response time lower than 200 milliseconds. When such analyzers are not available, it is possible to mix the expired air in a "mixing chamber" in order to average the concentrations of the two gases ($O_2$ and $CO_2$) making the fluctuations too slow to be accurately detected by the slow response time analyzers.

The "mixing chamber" analysis has however some great limitations:
it does not allow the detection of fast variations of the metabolic functions following sudden changes in the workload;
it does not allow for the analysis of the gas exchange corresponding to each breath, but only related to the average of several breaths; and
it does not allow the measurement of some important parameters such as $FetCO_2$ or VD/Vt.

Nowadays, although some portable systems for the measurements of metabolic parameters in real conditions are already available, none of those is able to provide measurements with the "breath by breath" technique.

The main reason for this lack is that oxygen analyzers with a fast response time (tr<200 msec) with dimensions and power consumption compatible with the requirements of a portable system are not available.

BRIEF SUMMARY OF THE INVENTION

The aim of the present invention is to provide a portable system for the monitoring of the metabolic parameters of an individual (oxygen uptake, carbon dioxide production, ventilation and heart rate) in real conditions without affecting significantly the physical performance using the "breath by breath" technique.

BRIEF DESCRIPTION OF THE DRAWINGS

The system according to the present invention will be described more in detail hereinbelow, according to the enclosed drawings in which a preferred embodiment is shown.

DETAILED DESCRIPTION OF THE INVENTION

Figure 1:
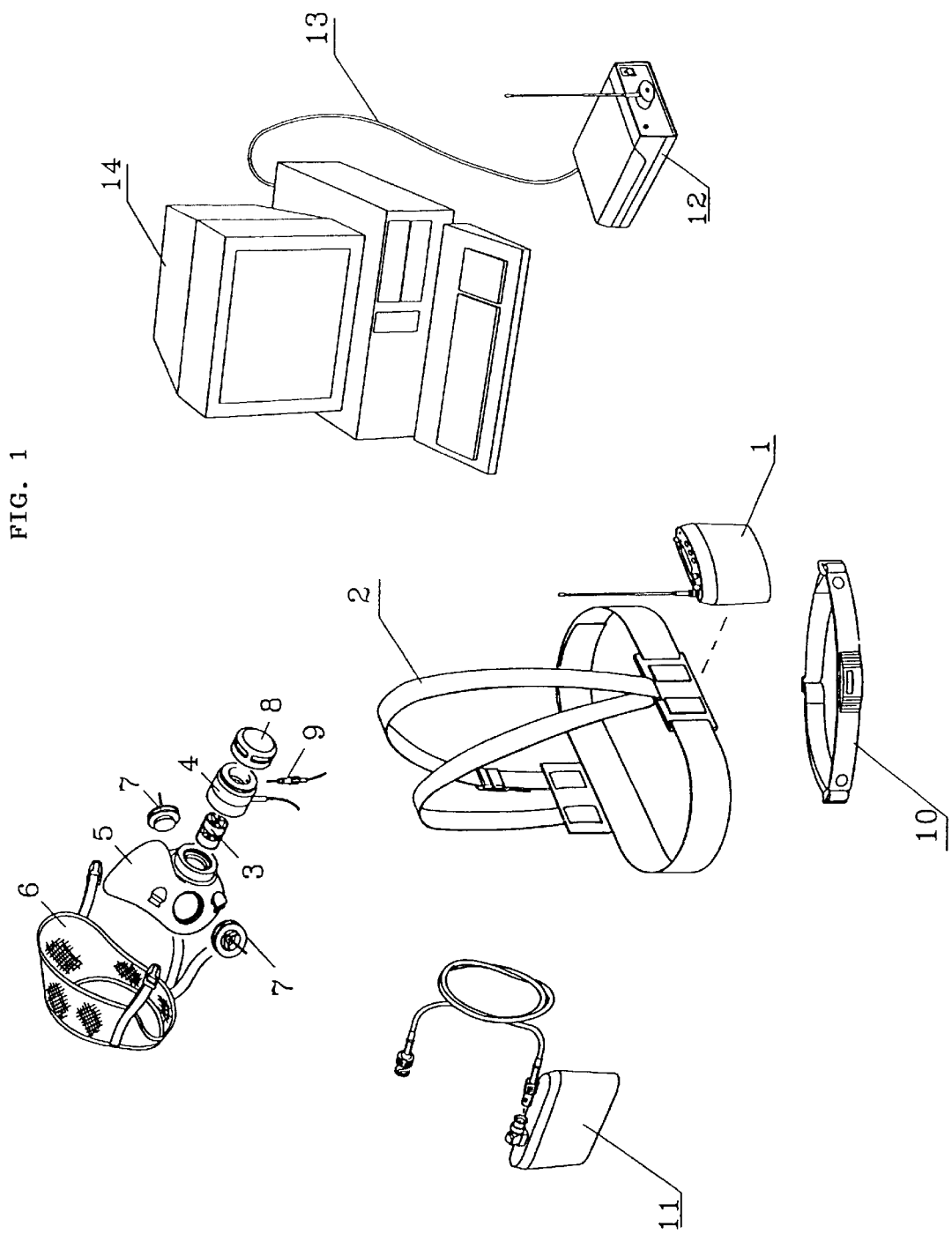
FIG. 1 shows an axonometric view and a partially exploded view of the main components of the system according to the present invention.

The enclosed figures show a portable system for the "breath by breath" measurement of the metabolic parameters of an individual, with telemetric data transmission and storage for further analysis, consisting of:
a portable unit 1, transported by the individual during the test fixed to an anatomic harness 2, incorporating a pump that samples continuously a fraction of the expired breath through a sampling line 9 connected near the mouth, bringing the gas into the analyzer ($O_2$ and $CO_2$) to provide the measurement of the oxygen and carbon dioxide concentrations; electrical signals coming from a turbine flowmeter 3-4-8 are elaborated to provide the measurement of the volumes of air ventilated by the individual; a detector circuit that receives the magnetic pulses transmitted by a heart monitor belt 10 to provide the heart rate; all the acquired signals are elaborated by the microprocessor incorporated in the portable unit and transmitted to a receiver unit 12 or stored in an internal non-volatile memory and transferred afterwards to a personal computer 14 for the analysis of the results; the portable unit 1 is powered by means of a rechargeable battery 11 fixed to the rear side of the harness in order to balance the weights;
a flowmeter 3-4-8, manufactured so that the ventilated air passing through a turbine 3, composed by two elycoidal conveyors which impress a rotation on it, proportional for its intensity to the flow and for its spin to the direction of the breath (inspiration/expiration); a blade, free to rotate on an axis parallel to the flow and perpendicular to the conveyors, assumes a rotation whose spin and intensity are measurable through the interruptions of the rays transmitted by three infrared diode emitters and received by as many receiving phototransistors; the pulsed signals coming from the optoelectronic reader 4 are acquired by the portable unit and elaborated; an aerodynamic cover 8, fixed to the front side of the flowmeter, is intended to avoid that, when the individual is moving during the test, the measurement of the ventilation is affected by the air entering the flowmeter;

a face mask 5-6-7, connected to the flowmeter, manufactured with antiallergenic material, provided with two inspiratory valves 7, whose task is to reduce the inspiratory resistance and to help the elimination of the sweat from the face, is fixed to the individual by means of an anatomic head cap 6;

a battery unit 11 that supplies the portable unit 1, is fixed to the rear side of the harness 2 so that the weights are balanced;

a heart monitor belt 10, provided with two electrodes to detect the electrical signals generated by the heart on the skin of the individual, incorporating an electronic circuit that amplifies the signals and transforms them into magnetic pulses corresponding to each beat; these pulses can be detected by the portable unit 1 wireless;

a receiver unit 12 that receives the results of the measurements transmitted by the portable unit via telemetric communication; this data, although transmitted, is however stored in the non-volatile memory of the portable unit and can be transferred to the personal computer once the test is completed.

Figure 2:
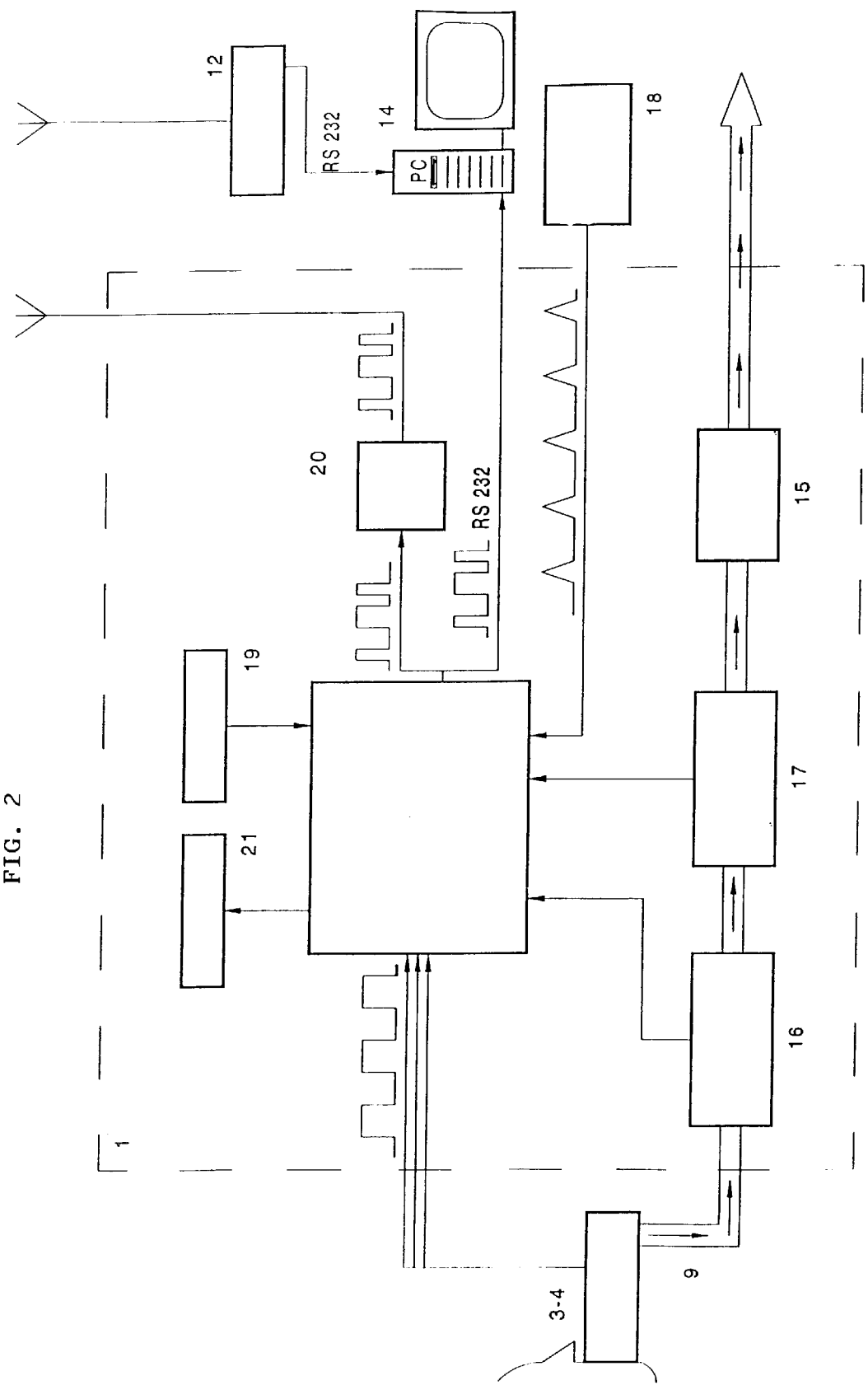
FIG. 2 shows the block diagram of electronic circuitry.

The main functions of the system can be described referring to the block diagram FIG. 2:

the expired gas of the individual is sampled by the line 9 connected at the output of the flowmeter 3-4; a miniaturized pump 15 provides the necessary depression to let the gas sample pass through the oxygen 16 and carbon dioxide 17 analyzers, connected in series in the pneumatic circuit, the output signals ($O_2$ and $C0_2$) are converted in numeric format and elaborated;

pulses coming from the flowmeter 3-4 are counted in order to obtain the measurement of the volume, and their width is measured for the flow calculation; since the pulses are distributed on three different lines corresponding to the three couples infrared emitter/receiver, determining the order by which those are detected, it is possible to provide the versus of the individual's breath (inspiration/expiration);

a detector probe 18, consisting of a coil and a conditioning circuit, detects the magnetic pulses transmitted by the heart rate belt 10 and provides electrical pulses which, counted by the microprocessor, allow the calculation of the heart rate;

all the operating procedures carried out during the normal use of the system (calibration, configuration, test execution . . . ) are managed by activating the keys of the keyboard 19 and controlling the messages prompted by the LCD display 21 or through the commands sent by the personal computer 14 via RS232, if eventually connected;

the results of the measurements of the test are stored in a non-volatile memory (flash memory) and in the meantime transmitted through the on board transmitter 20 to the receiver unit 12, connected to a personal computer 14 allowing the operator to control in real time the metabolic response of the individual under test;

the calculations used to obtain from the acquired signals (flow, $O_2$, $CO_2$ and HR) the main metabolic parameters ($VO_2$, $VCO_2$, RQ . . . ), are the same described in literature, however the particular elaboration of the oxygen concentration signal represents a particularity of this invention.

As formerly discussed, the response time of $O_2$ and $CO_2$ analyzers must be lower than 200 msec, for correctly carrying out the measurement with the "breath by breath" technique. The $CO_2$ analyzer 17, based on the infrared absorption technology, is fast enough to meet the specification.

The oxygen analyzer 16 instead, is a galvanic fuel cell and has an intrinsic response time of about 800 msec. The numeric elaboration performed on the $O_2$ concentration signal allows the dynamic response to "speed up" so as to obtain a response time lower than 130 msec.

Figure 3:
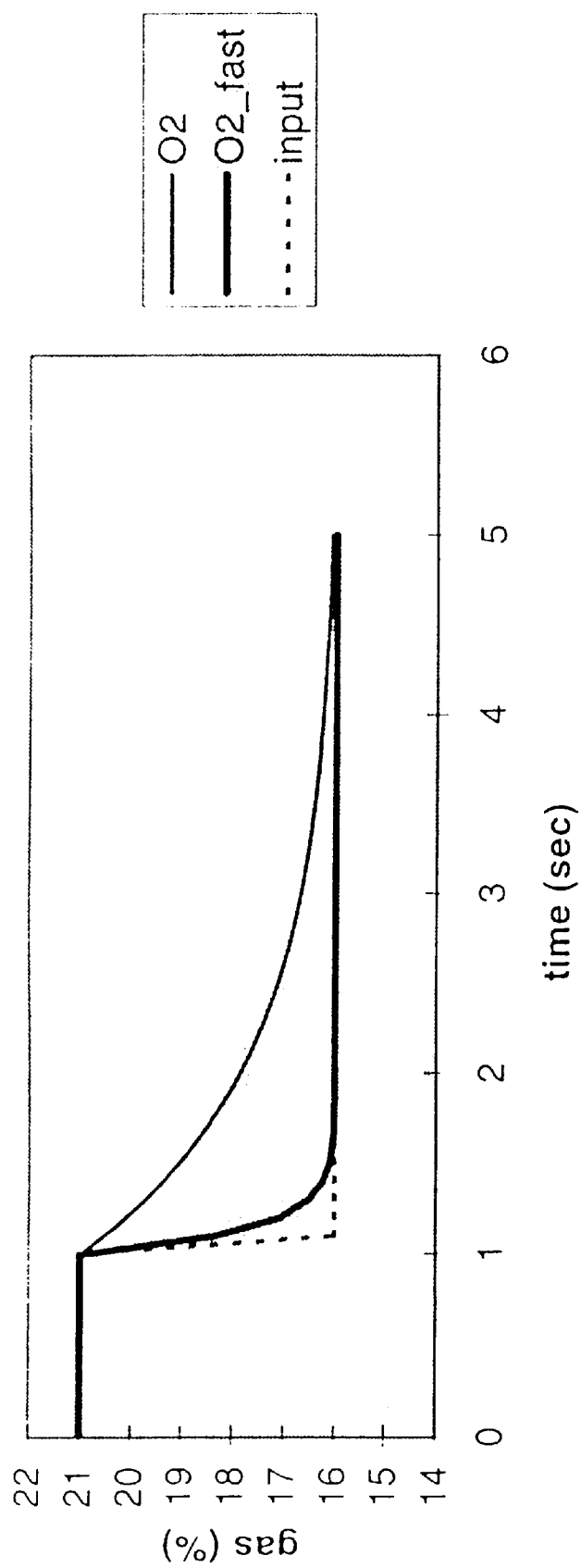
FIG. 3 shows a graph of the output of the oxygen sensor, following a step solicitation, before and after the numerical elaboration of the signal.

The graph of FIG. 3 shows the output signal of the oxygen sensor 16 following a step solicitation (obtained by suddenly turning the sampling line from room air to a calibration gas) before and after the elaboration; from the above mentioned plot, it is possible to verify that the combination of the low response oxygen sensor plus the numeric elaboration meets completely the requirements of the portable breath by breath metabolic system.

What is claimed is:

1. A portable system for breath-by-breath measurement of metabolic parameters of an individual, having telemetric data transmission and storage for later analysis, said portable system comprising:

a bidirectional turbine flowmeter comprising a turbine, an optoelectronic reader, and an aerodynamic cover, a portable unit, wherein said portable unit is transported by the individual during a test, is fixed to an anatomic harness, and is provided with an internal pump that samples continuously a fraction of expired breath through a sampling line connected near the mouth of the individual, bringing gas into an analyzer ($O_2$ and $CO_2$) to provide a measurement of oxygen and carbon dioxide concentrations, while electrical signals coming from said turbine flowmeter are elaborated to provide a measurement of the volumes of air ventilated by the individual;

a detector circuit which receives magnetic pulses transmitted by a heart monitor belt to provide a heart rate; and wherein all acquired signals are elaborated by a microprocessor incorporated in the portable unit, transmitted to a receiver unit, and stored in an internal non-volatile memory for transference after the test to a personal computer for result analysis purposes;

wherein said flowmeter is manufactured so that the ventilated air passing through the turbine, the turbine having two elycoidal conveyors, causes the turbine to rotate, proportional for its intensity to the flow and for its spin to the direction of the breath (inspiration/expiration);

wherein a blade, free to rotate on an axis parallel to the flow and perpendicular to the conveyors, assumes a rotations whose spin and intensity are measurable through interruptions of rays transmitted by three infrared diode emitters, and received by as many receiving phototransistors;

wherein the pulsed signals coming from the optoelectronic reader are acquired by the portable unit and elaborated; and wherein the aerodynamic cover, axed to the front side of the flowmeter, is intended to avoid that, when the individual is moving during the test, the measurement of the ventilation is affected by the air entering the flowmeter;

a face mask, connected to the flowmeter, manufactured with antiallergenic material, and having two inspiratory valves for reducing inspiratory resistance and for helping to eliminate sweat from the face of the individual, is fixed to the individual by means of an anatomic head cap;

a battery unit that supplies the portable unit, fixed to the rear side of the harness so that weights are balanced;

a heart monitor belt, having two electrodes to detect the electrical signals generated by the heart on the skin of the individual, and an electronic circuit that amplifies the signals and transforms the signals into magnetic pulses corresponding to each beat, wherein these pulses can be detected by the portable unit wireless; and a receiver unit that receives the results of the measurements transmitted by the portable unit via telemetric communication, wherein this data, although transmitted, is stored in the non-volatile memory of the portable unit and can be transferred to the personal computer once the test is completed.

2. A portable system according to claim 1, wherein the expired gas of the individual is sampled by the line connected at the output of the flowmeter, while a miniaturized pump provides for necessary depression to let the gas samples pass through the oxygen and carbon dioxide analyzers in series, in the pneumatic circuit, which continuously detect concentrations of $O_2$ and $CO_2$, while the output signals are converted in numeric format and elaborated by the microprocessor.

3. A portable system according to claim 1, wherein the pulses coming from the flowmeter are counted in order to obtain the measurement of the volume, and the width of the pulses is measured for flow calculation.

4. A portable system according to claim 1, wherein a detector probe, consisting of a coil and a conditioning circuit, detects the magnetic pulses transmitted by the heart rate belt, and provides electrical pulses which, counted by the microprocessor, allow calculation of the heart rate.

5. A portable system according to claim 1, wherein all the operating procedures carried out during normal use of the system including calibration, configuration, and test execution, are managed by at least one or two mode with the first including means for activating keys of a keyboard and controlling messages prompted by an LCD display and the second including means for sending comments by a personal computer.

6. A portable system according to claim 1, wherein the results of the measurements of the test are stored in a non-volatile memory (flash memory), and transmitted through an on board transmitter to the receiver unit, connected to a personal computer to allow an operator to control in real time the metabolic response of the individual under test.

7. A portable system according to claim 1, wherein the elaboration of the oxygen concentration signal, coming from a slow response time analyzer, speeds up dynamic response so as to obtain a response time lower than 130 msec.

8. A portable system for breath-by-breath measurement of metabolic parameters of an individual, having telemetric data transmission and storage for later analysis, said portable system comprising:

a bidirectional turbine flowmeter comprising a turbine, an optoelectronic reader, and an aerodynamic cover, a portable unit, wherein said portable unit, by way of an anatomic support, is transported by the individual during a test, and is provided with an internal pump that samples continuously a fraction of expired breath through a sampling line connected near the mouth of the individual, bringing gas into an analyzer to provide a measurement of oxygen and carbon dioxide concentrations, while electrical signals coming from said turbine flowmeter are elaborated to provide a measurement of the volumes of air ventilated by the individual, a heart rate detector circuit for monitoring a heart rate and generating a heart rate signal for use in an analysis of the metabolism parameters of the individual; and wherein all acquired signals are elaborated by a microprocessor incorporated in the portable unit for telemetric data transmission and storage for a later analysis option;

wherein said flowmeter is manufactured so that the ventilated air passing through the turbine cause the turbine to rotate proportional for its intensity to the flow and for its spin to the direction of the breath (inspiration/expiration);

wherein rotation characteristics of a rotating component of said turbine are measured by said optoelectronic reader, and pulsed signals coming from the optoelectronic reader are acquired by the portable unit and elaborated;

wherein the aerodynamic cover is positioned to avoid that, when the individual is moving during the test, the measurement of the ventilation is affected by the air entering said flowmeter;

a face mask for directing expired breath to said flowmeter;

a battery unit for powering the portable unit; and a receiver unit that receives the results of the measurements transmitted by the portable unit via telemetric communication, wherein this data, although transmitted, is also stored in a non-volatile memory of the portable unit and can be transferred to a personal computer once the test is completed.

9. A portable system according to claim 8, wherein the expired gas of the individual is sampled by the line connected at the output of the flowmeter, while a miniaturized pump provides for necessary depression to let the gas samples pass through the oxygen and carbon dioxide analyzers in series, in the pneumatic circuit, which continuously detect concentrations of $O_2$ and $CO_2$, while the output signals are converted into a format for elaboration by the microprocessor.

10. A portable system according to claim 8, wherein pulses coming from the flowmeter are counted in order to obtain the measurement of the volume, and a width of the pulses is measured for flow calculation.

11. A portable system according to claim 8, further comprising a heart monitor belt and wherein a detector probe, consisting of a coil and a conditioning circuit, detects the magnetic pulses transmitted by the heart rate belt of said, and provides electrical pulses which, counted by the microprocessor, allow calculation of the heart rate.

12. A portable system according to claim 8, wherein the results of the measurements of the test are stored in a non-volatile memory (flash memory), and transmitted through an on board transmitter to the receiver unit, connected to a personal computer to allow an operator to control in real time the metabolic response of the individual under test.

13. A portable system according to claim 8, wherein the elaboration of the oxygen concentration signal, coming from a slow response time analyzer, speeds up dynamic response so as to obtain a response time to a level that provides for breath by breath measurement.

14. A portable system according to claim 13 wherein the response time is lower than 130 msec.

* * * * *